United States Patent [19]

Diana

[11] 4,372,976
[45] Feb. 8, 1983

[54] NOVEL ARYL-ALIPHATIC KETONE AND ITS USE AS AN ANTIVIRAL AGENT

[75] Inventor: Guy D. Diana, Stephentown, N.Y.

[73] Assignee: Sterling Drug Inc., New York, N.Y.

[21] Appl. No.: 291,015

[22] Filed: Aug. 7, 1981

[51] Int. Cl.³ .................... A61K 31/12; C07C 49/252
[52] U.S. Cl. .................................... 424/331; 568/325
[58] Field of Search ................ 568/325, 329; 424/331

[56] References Cited

U.S. PATENT DOCUMENTS 3,917,718  11/1975  Collins ............................ 260/613 R
4,096,280   6/1978  Diana et al. ........................ 568/325
4,171,365  10/1979  Diana et al. ........................ 568/325

OTHER PUBLICATIONS

Astoin, Chem. Abst., vol. 89, #359m, (1978).

*Primary Examiner*—James H. Reamer
*Attorney, Agent, or Firm*—Thomas L. Johnson; B. Woodrow Wyatt

[57] ABSTRACT

A novel antiviral agent, tert-butyl (3,4-dibenzyloxy)styryl ketone, is described.

3 Claims, No Drawings

NOVEL ARYL-ALIPHATIC KETONE AND ITS USE AS AN ANTIVIRAL AGENT

BACKGROUND OF THE INVENTION a. Field of the Invention

The invention relates to a novel ketone, namely tert-butyl (3,4-dibenzyloxy)styryl ketone and to compositions and method for the use thereof as an antiviral agent.

b. Description of the Prior Art

Collins U.S. Pat. No. 3,917,718, issued Nov. 4, 1975, discloses cyclopropyl (3,4-dibenzyloxy)styryl ketone (column 10, line 26), there stated to be active against equine rhinovirus at 1.5 micrograms per milliliter.

SUMMARY OF THE INVENTION

In a composition of matter aspect the invention relates to the novel compound, tert-butyl (3,4-dibenzyloxy)styryl ketone.

In a further composition of matter aspect the invention relates to a composition for combatting viruses which comprises an antivirally effective amount of tert-butyl (3,4-dibenzyloxy)styryl ketone in admixture with a suitable carrier or diluent.

In a process aspect, the invention relates to a process for combatting viruses which comprises contacting the locus of said viruses with an antivirally effective amount of tert-butyl (3,4-dibenzyloxy)styryl ketone.

DETAILED DESCRIPTION INCLUSIVE OF PREFERRED EMBODIMENTS tert-Butyl (3,4-dibenzyloxy)styryl ketone having the formula

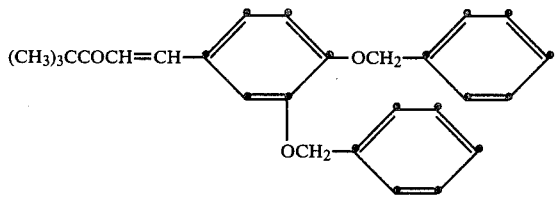

is prepared by reacting tert-butyl methyl ketone with 3,4-dibenzyloxybenzaldehyde in the presence of a strong base. The procedural details of the preparation are given in the following example.

EXAMPLE tert-Butyl (3,4-dibenzyloxy)styryl ketone

To a suspension of 9.13 g (0.0913 m) of tert-butyl methyl ketone and 29 g (0.0913 m) of 3,4-dibenzyloxybenzaldehyde in 75 ml of ethanol was added dropwise 8.95 ml of 20 % aqueous sodium hydroxide. The reaction mixture was warmed at 40° C. for 18 hours, 25 ml of water was then added, and the mixture was stirred at 40° C. for 18 hours longer. Upon cooling the mixture, a heavy gum separated which was triturated with water and pentane. Slow addition of methanol caused the gum to crystallize. The crystals were filtered, washed with water and pentane, and recrystallized from ethanol. The resulting product was washed with pentane and dried at 40° C. in vacuo for 22 hours to give 12.4 g of tert-butyl (3,4-dibenzyloxy)styryl ketone as a yellow solid, m.p. 80°–83° C.

Anal. Calcd. for $C_{27}H_{28}O_3$: C, 80.97; H, 7.04. Found: C, 80.81; H, 6.97.

Biological evaluation of the compound of the invention has shown that it possesses antiviral activity. The intended use of the compound is in combatting viruses present on inanimate surfaces as well as topical treatment of viral infections in animal organisms. The in vitro testing of the compound of the invention by standard serial dilution procedures has shown that it possesses antiviral activity against a variety of virus species. In the following table the activity of tert-butyl (3,4-dibenzyloxy)styryl ketone is given in terms of minimum inhibitory concentration (MIC) in micrograms per milliliter.

| Virus | MIC |
| --- | --- |
| Rhinovirus type 2 | 3–1.5 mcg/ml |
| Rhinovirus type 14 | 6–3 mcg/ml |
| Equine rhinovirus | 6–3 mcg/ml |
| Parainfluenza type 3 | 3 mcg/ml |

The antiviral compositions are formulated by preparing a dilute solution or suspension in an aqueous, organic or aqueous-organic medium, for example ethyl alcohol, acetone, dimethyl sulfoxide, and the like; and are applied to the locus to be disinfected by conventional means such as spraying, swabbing or immersing. Alternatively, the compound can be formulated as ointments or creams by incorporating it in conventional ointment or cream bases, such as alkylpolyether alcohols, cetyl alcohol, stearyl alcohol and the like; as jellies by incorporating it in conventional jelly bases such as glycerin and tragacanth; or as aerosol sprays or foams. The antivirally effective component of the composition is present in a concentration of between about 1 part per million and about 5 percent by weight, depending upon the object to be treated and the type of formulation employed. For disinfection of inanimate surfaces with aqueous or aqueous-organic solutions, concentrations in the lower part of the range are effective. For topical application in medical or veterinary use in the form of ointment, cream, jelly or aerosol, concentrations in the upper part of the range are preferred.

I claim:

1. tert-Butyl (3,4-dibenzyloxy)styryl ketone.
2. A composition for combatting viruses which comprises an antivirally effective amount of tert-butyl (3,4-dibenzyloxy)styryl ketone in admixture with a suitable carrier or diluent.
3. A process for combatting viruses which comprises contacting the locus of said viruses with an antivirally effective amount of tert-butyl (3,4-dibenzyloxy)styryl ketone.

* * * * *